(12) United States Patent
White

(10) Patent No.: US 8,523,949 B2
(45) Date of Patent: *Sep. 3, 2013

(54) EXTRACAPSULAR SURGICAL PROCEDURE AND SURGICAL REFERENCING INSTRUMENT THEREFOR

(76) Inventor: Ralph Richard White, Portland, OR (US)

(*) Notice: Subject to any disclaimer, the term of this patent is extended or adjusted under 35 U.S.C. 154(b) by 215 days.

This patent is subject to a terminal disclaimer.

(21) Appl. No.: 13/022,481

(22) Filed: Feb. 7, 2011

(65) Prior Publication Data

US 2011/0125161 A1 May 26, 2011

Related U.S. Application Data

(60) Division of application No. 11/221,097, filed on Sep. 6, 2005, now Pat. No. 7,905,924, which is a continuation-in-part of application No. 10/934,269, filed on Sep. 3, 2004, now abandoned.

(60) Provisional application No. 60/499,859, filed on Sep. 3, 2003.

(51) Int. Cl.
A61F 2/30 (2006.01)

(52) U.S. Cl.
USPC .................. 623/18.11; 623/914; 623/13.11

(58) Field of Classification Search
USPC ................. 623/18.11, 914, 13.11–13.2
See application file for complete search history.

(56) References Cited

U.S. PATENT DOCUMENTS

| 1,235,715 | A | | 8/1917 | Mooney |
| 1,250,259 | A | | 12/1917 | Westlin |
| 1,849,959 | A | | 3/1932 | Schneider |
| 1,889,239 | A | | 11/1932 | Crowley |
| 2,002,021 | A | | 5/1935 | Rouse |
| 2,181,746 | A | | 11/1939 | Siebrandt |
| 3,709,219 | A | | 1/1973 | Halloran |
| 4,098,269 | A | | 7/1978 | Judet |
| 4,632,100 | A | | 12/1986 | Somers et al. |
| 4,708,139 | A | | 11/1987 | Dunbar, IV |
| 4,712,542 | A | | 12/1987 | Daniel et al. |
| 4,772,286 | A | | 9/1988 | Goble et al. |
| 4,907,577 | A | | 3/1990 | Wu |
| 5,037,426 | A | * | 8/1991 | Goble et al. ............ 606/96 |
| 5,112,337 | A | | 5/1992 | Paulos et al. |
| 5,156,161 | A | | 10/1992 | Lollar |
| 5,210,955 | A | | 5/1993 | Lewis |
| 5,443,465 | A | | 8/1995 | Pennig |

(Continued)

OTHER PUBLICATIONS

Kuroda, R. et al "Localization of growth factors in the reconstructed anterior cruciate ligament: immunohistological study in dogs", Knee Surg Sports Traumatol Arthrosc 2000;8(2): 120-6 (abstract only), retrieved online on Aug. 18, 2004.*

(Continued)

Primary Examiner — Paul Prebilic
(74) Attorney, Agent, or Firm — Lane Powell PC

(57) ABSTRACT

A method and device for finding isometric points in the joints of mammals for use in surgical repair of a joint. Isometric points are first identified in radiographic or other two dimensional images and then located in the actual joint. A method for repairing a cruciate ligament-deficient canine stifle employing the method and device for finding isometric points is described. A method and apparatus for locating the axis of rotation of a joint is also described.

2 Claims, 10 Drawing Sheets

(56) References Cited

U.S. PATENT DOCUMENTS

| | | | |
|---|---|---|---|
| 5,564,437 A * | 10/1996 | Bainville et al. | 600/587 |
| 5,570,706 A | 11/1996 | Howell | |
| 5,743,909 A | 4/1998 | Collette | |
| 5,968,051 A | 10/1999 | Luckman et al. | |
| 6,214,014 B1 | 4/2001 | McGann | |
| 6,383,200 B1 | 5/2002 | Wotton, III | |
| 6,395,010 B1 | 5/2002 | Wotton, III | |
| 8,317,862 B2 * | 11/2012 | Troger et al. | 623/13.11 |
| 2001/0027344 A1 * | 10/2001 | Bonutti | 623/13.17 |
| 2002/0120280 A1 * | 8/2002 | Wotton, III | 606/148 |
| 2004/0105086 A1 * | 6/2004 | Leitner et al. | 356/3 |
| 2008/0125678 A1 * | 5/2008 | Breen | 600/595 |
| 2008/0243127 A1 * | 10/2008 | Lang et al. | 606/87 |

OTHER PUBLICATIONS

Beale, B.S. "What's New in Anterior Cruciate Ligament Repair", 1999 North American Veterinary Conference Proceedings Abstract, retrieved online on Apr. 30, 2002.*

Gahring, Dean R., "Management of the Cranial Criciate Ligament-Deficient Large Dog Utitilizing Tibial Plateau Leveling Osteotomy (TPLO)", retrieved online on Jun. 17, 2002.*

Kleiner et al, "The phenomenon of 'ligamentization': anterior cruciate ligament reconstruction with autogenous patellar tendon", J Orthop Res. 1986; 4(2):162-72 (abstract only) retrieved online on Aug. 8, 2004.*

Kurosaka, M. et al, "A biomedical comparison of different surgical techniques of graft fixation in anterior cruciate ligament reconstruction", Am J Sports Med. 1987, May-Jun.; 15(3): 225-9, (abstract only), retrieved online on Aug. 7, 2004.*

Leduc S. et al "Mechanical evaluation of a ligament fixation system for ACL reconstruction at the tibia in a canine cadaver model", Ann Chir 1999; 53(8):735-41, (abstract only) retrieved online on Aug. 18, 2004.*

Selmi et al, "The Lemaire extra-articular Reconstruction", Maltrise Orthopedique publications, No. 60, Jan. 1997, pp. 1-27 (4 page summary only).*

St Kudnig, "Intra-articular replacement", retrieved online on Jul. 14, 2004.*

Biomechanical analysis of human ligament grafts used in knee-ligament; Mar. 1984.

Vasseur PB, Rodrigo JJ, Stevenson S, Clark G, Sharkey N; Replacement of the Anterior Cruciate Ligament with a Bone-Ligament-Bone Anterior Cruciate Ligament Allograft in Dogs; Jun. 1987.

Melhorn JM, Henning CE; The Relationship of the Femoral Attachment site to the Isometric Tracking of the Anterior Cruciate Ligament Graft; Nov.-Dec. 1987.

Patterson RH, Smith GK, Gregor TP, Newton CD; Biomechanical Stability of Four Cranial Cruciate Ligament Repair Techniques in the Dog; Mar.-Apr. 1991.

E. Marlowe Goble, M.D.; Fascia Lata Allograft and Fluoroarthroscopic ACL Reconstruction; Feb. 1992.

Kasperczyk WJ, Bosch U, Oestern HJ, Tscherne H; Staging of Patellar Tendon Autograft Healing After Posterior Cruciate Ligament Reconstruction. A Biomechanical and Histological Study in a Sheep Model; Jan. 1993.

Lane JG, McFADDEN P, Bowden K, Amiel D; The Ligamentization Process: a 4 Year Case Study Following ACL Reconstruction with a Semitendinosis Graft; Apr. 1993.

Goertzen MJ, Clahsen H, Burrig KF, Schulitz KP; Sterilisation of Canine Anterior Cruciate Allografts by Gamma Irradiation in Argon. Mechanical and Neurohistological Properties Retained One Year After Transplantation; Mar. 1995.

Moore KW, Read RA; Cranial Cruciate Ligament Rupture in the Dog—a Retrospective Study Comparing Surgical Techniques; Aug. 1995.

Tohyama H, Beynnon BD, Johnson RJ, Renstrom PA, Arms SW; The Effect of Anterior Cruciate Ligament Graft Elongation at the Time of Implantation on the Biomechanical Behavior of the Graft and Knee; Sep.-Oct. 1996.

Nachtkamp J, Klosterhalfen B, Pott S, Magin MN, Paar O; [Ligamentization as an Explanation for the Stability of Periosteal Flap Repair in the Replacement of the Fibular Ligament System]; Nov. 1997.

Kobayashi D, Kurosaka M, Yoshiya S, Mizuno K; Effect of Basic Fibroblast Growth Factor on the Healing of Defects in the Canine Anterior Cruciate Ligament; Sep. 1997.

Falconiero RP, DiStefano VJ, Cook TM; Revascularization and Ligamentization of Autogenous Anterior Cruciate Ligament Grafts in Humans; Mar. 1998.

Mark G. Siegel, M.D., and Sue D. Barber-Westin, B.S.; Arthroscopic-Assisted Outpatient Anterior Cruciate Ligament Reconstruction Using the Semitendinosus and Gracilis Tendons; Apr. 1998.

Scranton PE JR, Lanzer WL, Ferguson MS, Kirkman TR, Pflaster DS; Mechanisms of Anterior Cruciate Ligament Neovascularization and Ligamentization; Oct. 1998.

Nordt WE, Lotfi P, Plotkin E, Williamson B; Am J Sports Med; Sep. 1999.

Bellelli A, Adriani E, Margheritini F, Camillieri G, Della Rocca C, Mariani PP; Radiol Med; Dec. 1999.

Goradia VK, Rochat MC, Kida M, Grana WA; Natural History of a Hamstring Tendon Autograft Used for Anterior Cruciate Ligament Reconstruction in a Sheep Model; Jan.-Feb. 2000.

Boyd SK, Matyas JR, Wohl GR, Kantzas A, Zernicke RF; J Appl Physiol; Dec. 2000.

Stork CK, Gibson NR, Owen MR, Li A, Schwarz T, Bennett D, Carmichael S; Radiographic Features of a Lateral Extracapsular Wire Suture in the Canine Cranial Cruciate Deficient Stifle; Oct. 2001.

Muellner T, Kwasny O, Lochnert V, Mallinger R, Unfried G, Schabus R, Plenk H JR; Light and Electron Microscopic Study of Stress-Shielding Effects on Rat Patellar Tendon; Nov. 2001.

Tisha Adele Maria Harper; A Biomechanical Cadaver Study to Determine the Effectiveness of the Lateral Graft Technique and Isometric Suture Placement for Extracapsular Stabilization of the Cranial Cruciate Ligament Deficient Stifle in the Dog; Mar. 2003.

Chen CH, Chen WJ, Shin CH, Yang CY, Liu SJ, Lin PY; Enveloping the Tendon Graft with Periosteum to Enhance Tendon-Bone Healing in a Bone Tunnel: A Biomechanical and Histologic Study in Rabbits; Mar. 2003.

Soda Y, Sumen Y, Murakami Y, Ikuta Y, Ochi M; Attachment of Autogenous Tendon Graft to Cortical Bone is Better than to Cancellous Bone: a Mechanical and Histological Study of MCL Reconstruction in Rabbits; Jun. 2003.

Lopez MJ, Markel MD, Kalscheur V, Lu Y, Manley PA; Hamstring Graft Techniques for Stabilization of Canine Cranial Cruciate Ligament Deficient Stifles; Jul.-Aug. 2003.

Greg Harasen; Canine Cranial Cruciate Ligament Rupture in Profile; Oct. 2003.

Daniel A. Degner, DVM; The Dynamic Tibial Plateau Leveling PR.. Novel Surgery for Cranial Cruciate Liga . . . Immature Dogs; Dec. 2003.

Max Nielsen Banwell; In Vitro Evaluation of the Securos Cranial Cruciate Ligament Repair System and Fluorocarbon Leader Line for use as Lateral Fabella-Tibial Sutures; May 2004.

Togachefsky RA, Altman RD, Markov MS, Cheung HS; Bioelectromagnetics; May 2004.

* cited by examiner

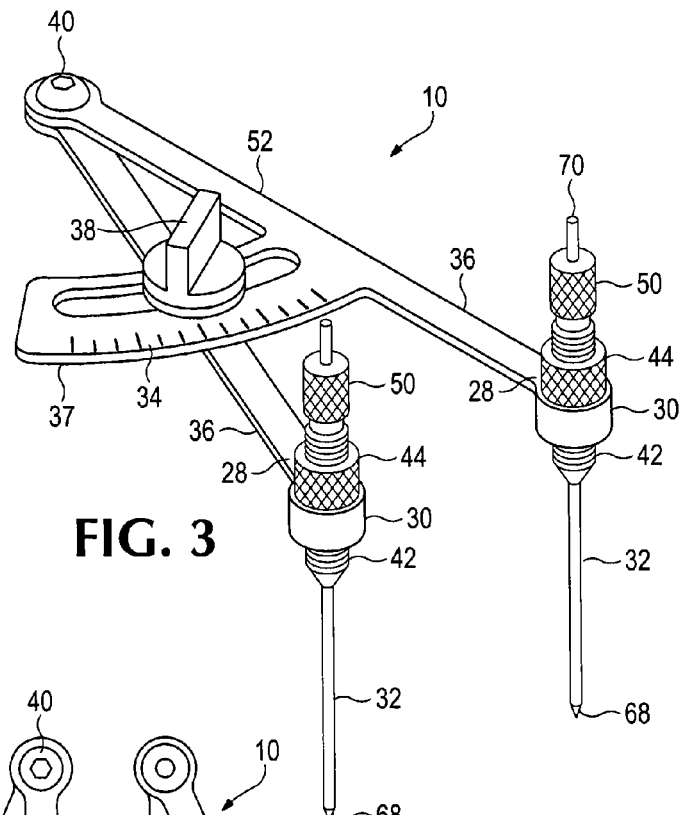
FIG. 3
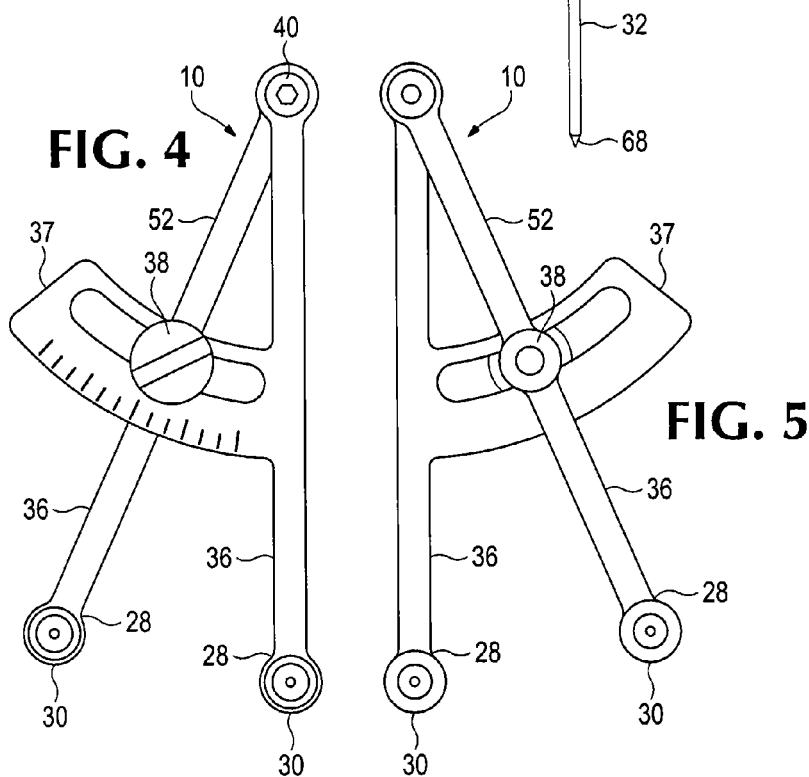
FIG. 4
FIG. 5

EXTRACAPSULAR SURGICAL PROCEDURE AND SURGICAL REFERENCING INSTRUMENT THEREFOR

CROSS-REFERENCE TO RELATED APPLICATIONS

This application is a division of U.S. patent application Ser. No. 11/221,097, filed Sep. 6, 2005, now U.S. Pat. No. 7,905,924, which is a continuation-in-part of U.S. patent application Ser. No. 10/934,269, flied Sep. 3, 2004, now abandoned, which application claims the benefit of U.S. Provisional App. No. 60/499,859, filed Sep. 3, 2003.

BACKGROUND OF THE INVENTION

This application relates to surgery for repair of injured articulating joints between bones in mammals, and to a method and a device for use therein.

The caudal and cranial cruciate ligaments are the primary stabilizers of the stifle joint in mammals such as canines. The caudal cruciate ligament originates from the lateral side of the medial femoral condyle and inserts on the medial aspect of the popliteal notch of the tibia. The cranial cruciate ligament originates from the medial side of the lateral femoral condyle and inserts on the cranial medial tibial plateau. In canines, the stifle joint is normally capable of flexion and extension with a 110 degree range of motion, varus and valgus angulation, and internal and external rotation. The stifle is extended by the quadriceps muscle group. Injury to a cruciate ligament will commonly result in destabilization of the joint. The joint must be surgically stabilized following such an injury.

Current surgical techniques for anterior cruciate ligament replacement and/or stabilization in canine knee or stifle joints are grouped into extracapsular procedures and intracapsular procedures. Intracapsular procedures require a graft from an adjacent tissue such as the straight patellar tendon or the fascia lata, which is detached from its origin and inserted or repositioned through tunnels bored in the distal femur and/or proximal tibia. This surgery is done inside the joint capsule, with both ends of the transplant being fixed to the walls of the tunnels and/or adjacent bone. Extracapsular procedures use tissues or suture implants placed outside of the joint capsule in order to stabilize the joint.

Determination of the isometric relationship between location of the origin and location of the insertion of a ligament repair structure forms the foundations of intracapsular surgical repair of ligaments in humans. These same isometric relationships may be determined and used for extracapsular repair of cruciate or other ligament failure in the joints of any mammal. However, current extracapsular surgical procedures have not addressed the optimal placement of transplant tissue or suture at the isometric points.

What is needed then is a surgical device and procedure for repair of a ligament that provides for the determination of optimal points for the attachment of graft, transplant, or other tissues or tension-bearing materials in an extracapsular procedure.

SUMMARY OF THE INVENTION

As a first aspect of a method according to the disclosure herein, a device and method for determining spatial relationships in a joint of a mammal comprises obtaining two-dimensional images of the joint in flexed and extended positions, finding a reference point on one bone of the joint and at least approximately locating an isometric point on another bone in the joint by using the two dimensional images, and thereafter using a measuring and positioning device to locate those points in the mammal joint.

According to another aspect of the disclosure herein a locating and positioning device is provided by means of which a reference point can be marked on a first bone of a joint and an isometric point can be located and verified. As another aspect of the method disclosed the locating and positioning device can be used to aid in establishing a hole in at least the second bone to receive a tissue anchor as part of a graft-forming procedure.

In accordance with an aspect of the device, the locating and positioning device can be adjusted and fastened to measure spacing between a pair of locating portions.

As a feature of one embodiment of the device the locating portions are carried as the distal ends of respective area of a pair of arms adjustably pivotable with respect to each other, and at least one of the locating portions is adjustable with respect to the arm on which it is carried.

In accordance with one aspect of a method of using the locating and positing device one locating portion can be fastened to one of a pair of bones that meet in an articulating joint, and the other locating portion can be moved relative to the first to find and verify the location of an axis of rotation of a joint that can move in a hinge-like fashion, in order to determine where to place an external fixation device for use in supporting such a joint during the process of healing after an injury to the joint.

The foregoing and other objectives, features, and advantages of the invention will be more readily understood upon consideration of the following detailed description, taken in conjunction with the accompanying drawings.

BRIEF DESCRIPTION OF THE SEVERAL VIEWS OF THE DRAWINGS

FIG. 3 is an isometric view of a measuring and positioning device which is an exemplary embodiment of one aspect of the present invention.

FIG. 4 is a top plan view of the device shown in FIG. 3.

FIG. 5 is a bottom plan view of the device shown in FIG. 3.

DETAILED DESCRIPTION OF PREFERRED EMBODIMENTS

Figure 1:
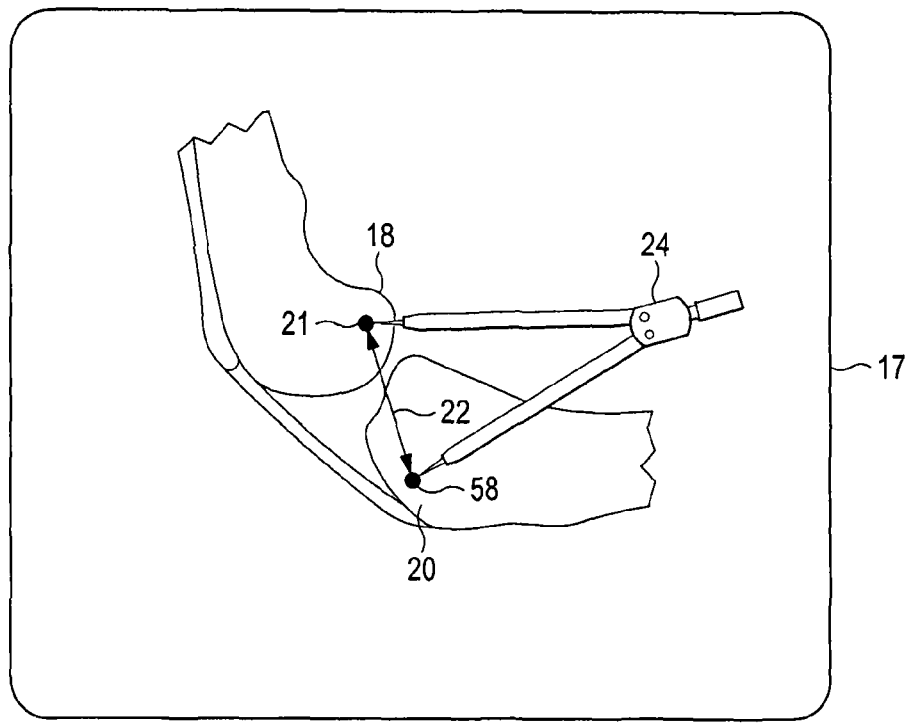
FIG. 1 is a view of a radiograph of a canine stifle joint in a fully flexed position, showing use of a pair of dividers to measure a distance between respective points on the tibia and femur shown in the radiograph.

In a typical articulated joint, the ends of the bones which meet in the joint operate as cams such that when the joint is flexed and extended the distance between a given first point in a first bone and a second point on the second bone changes depending on the degree of flexion and extension. However, points typically exist in joints that have what can be described as an isometric relationship. The distance between a given point on one bone and its isometric point on the second bone changes during flexion and extension but is the same at full flexion and full extension. Such points can be said to have an isometric relationship, and herein will be referred to as isometric points. When connective structures such as cruciate ligaments in a joint are damaged and grafts or other replacement or substitute structures are employed to repair the joint, these replacement structures should ideally be fastened to points which have such an isometric relationship, in order to facilitate the proper function of the joint. When the replacement structure is attached at such isometric points, it is under equal tension at each limit of normal range of motion of the joint after surgical repair.

Referring to the drawings, which form a part of the disclosure herein, a measuring and locating device and a method for its use as disclosed herein permit a surgeon to locate appropriate isometric points in articulated mammal joints, optimally after those points have been previously approximated or identified in radiographic or other two-dimensional images of the joint. A method of repairing a torn cranial cruciate ligament, a relatively frequent and significantly debilitating injury occurring in the stifle or knee joint in canines, and use of such a measuring and locating device to repair a cranial cruciate ligament in a dog's stifle joint is explained herein. The device and method may also be used to locate isometric points in any mammalian joint. The device and method may also be used to locate other medically relevant points, such as in locating an axis of rotation of a hinged or ginglymus type joint of any mammal.

In placement of a replacement structure such as a graft, suture, or other structure in a joint, a first point of attachment of a replacement structure must be determined. In the exemplary surgical procedure described below, the joint to be repaired is a stifle, or knee, joint of a canine, although the procedure is generally the same in the stifle or knee of other mammals, and the device can be used to find medically relevant points in many other mammalian joints. As shown herein, the replacement structure to compensate for a torn anterior cranial cruciate ligament is an autograft 12 composed of a portion of the fascia lata and the cranial insertion of the biceps femoris muscle. These structures insert naturally at Gerdy's Tubercle 20. The combined insertions of the fascia lata and cranial insertion of the biceps femoris muscle on Gerdy's Tubercle form a strong, dynamic, vascularized ligamentous insertion at this tubercle. Because these structures are already attached to the tibia at Gerdy's Tubercle, and because Gerdy's Tubercle has an isometric relationship with a point on the lateral femoral condyle, Gerdy's Tubercle is a logical first point of attachment for the replacement structure employed in this particular surgery. The preferred points of attachments to be used may vary in other situations, depending on the joint, the surgical technique used, the nature of the replacement structure employed, and other factors.

An isometric point on the lateral femoral condyle 18 is a logical choice for the second point of attachment when Gerdy's Tubercle is used as a first point of attachment. In the frontal plane and sagittal planes, the line defined by the origin and insertion of the CCL lies approximately parallel to a line drawn from Gerdy's Tubercle to the isometric point on the lateral femoral condyle. The dorsal view of the stifle joint shows that the origin and insertion of the cranial cruciate ligament roughly parallels the line drawn between Gerdy's Tubercle and the determined isometric point on the femoral condyle. Therefore, an autograft attached at these points can function well to stabilize the stifle.

The first step repairing such an injured stifle is to prepare full scale or known scale latero-medial radiographic or other two-dimensional images of the joint to be stabilized. See FIGS. 1 and 2. It is preferable to take radiographic images of both corresponding joints for comparison. For example, where a dog's stifle is to be repaired, images should be taken of both the dog's stifles. Images are taken with the joint in at least two positions in its range of motion, preferably in full extension as shown in radiograph 19, FIG. 2, and in full flexion as shown in radiograph 17, FIG. 1.

Figure 2:
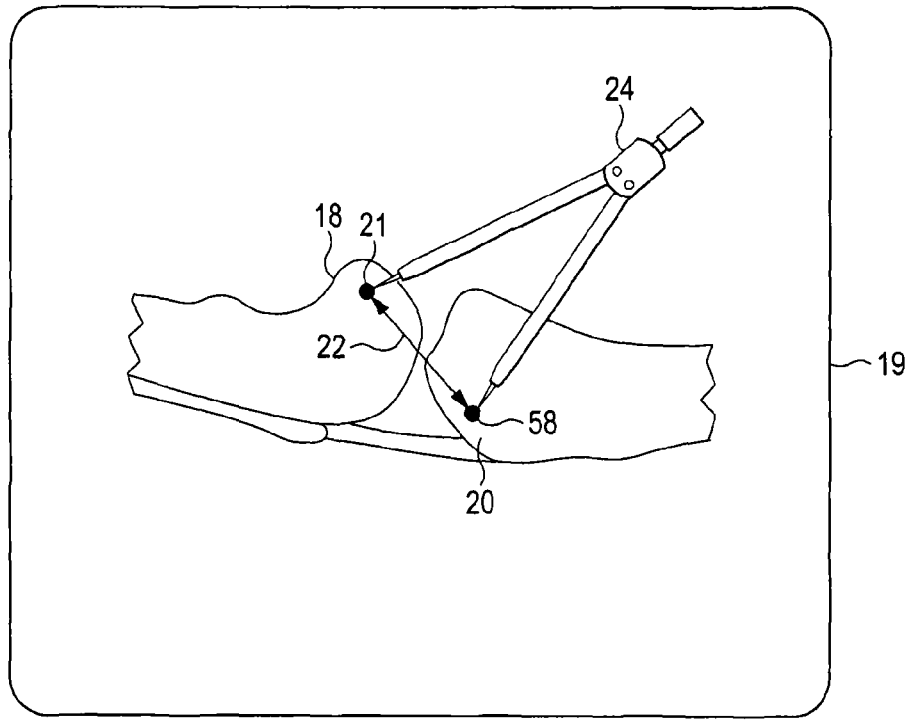
FIG. 2 is a view of a radiograph of the same stifle joint shown in the radiograph depicted in FIG. 1, with the stifle joint in its fully extended position, showing use of a divider to measure between a selected point on the tibia and a point on the femur shown in the radiograph.
Figure 6:
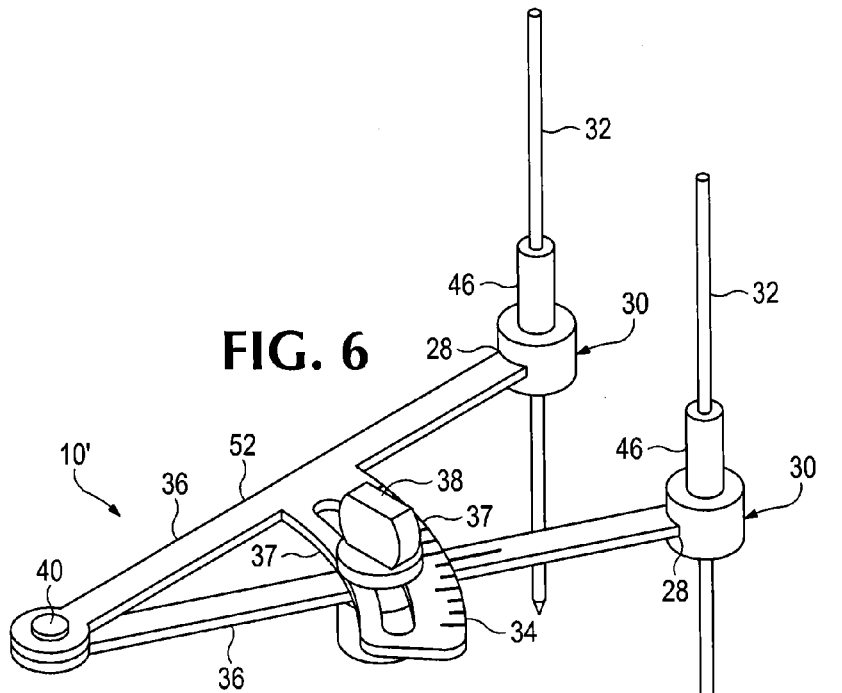
FIG. 6 is an isometric view of a measuring and positioning device which is another exemplary embodiment of an aspect of the disclosure herein.
Figure 7:
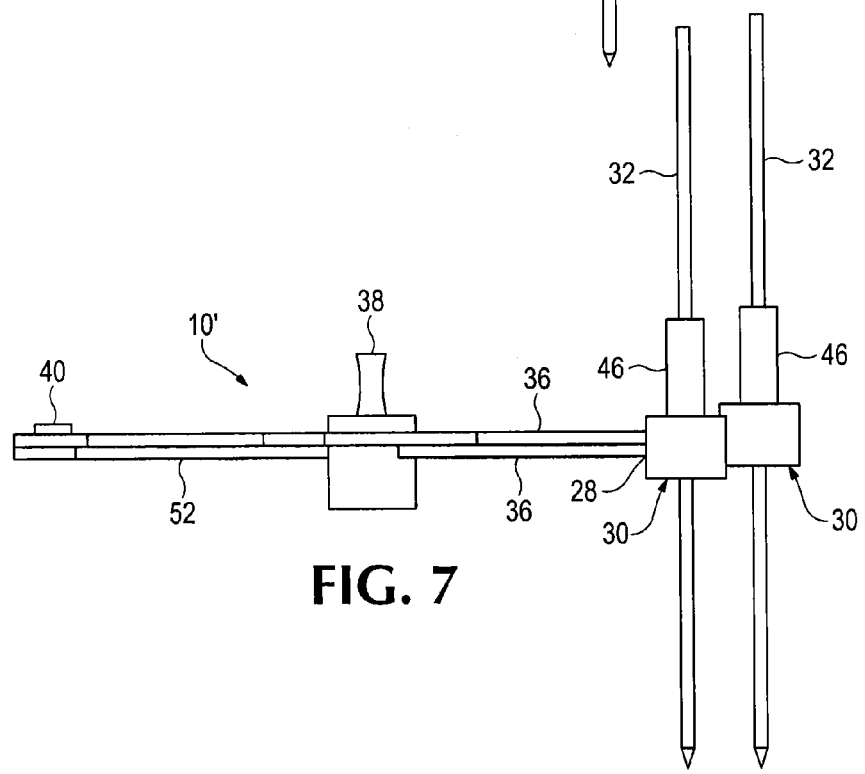
FIG. 7 is a side elevational view of the device shown in FIG. 6.
Figure 8:
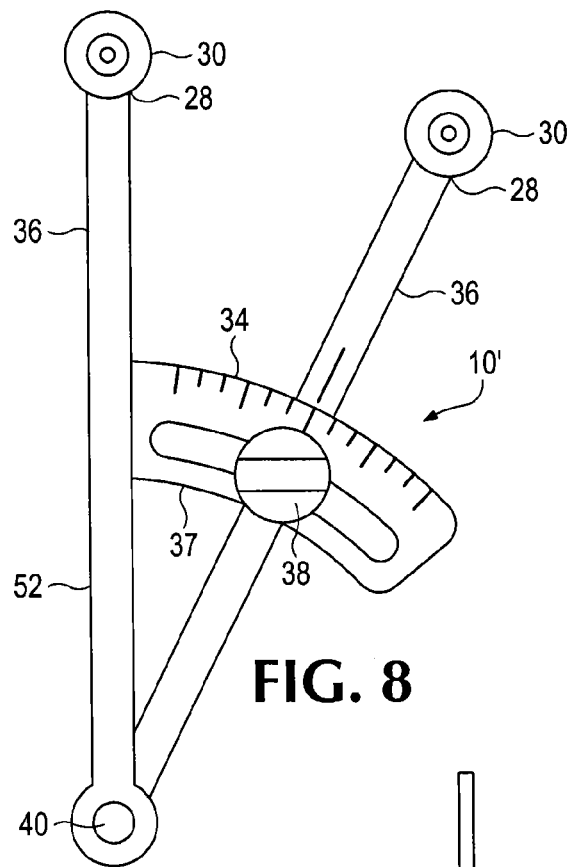
FIG. 8 is a top plan view of the device shown in FIG. 6.
Figure 9:
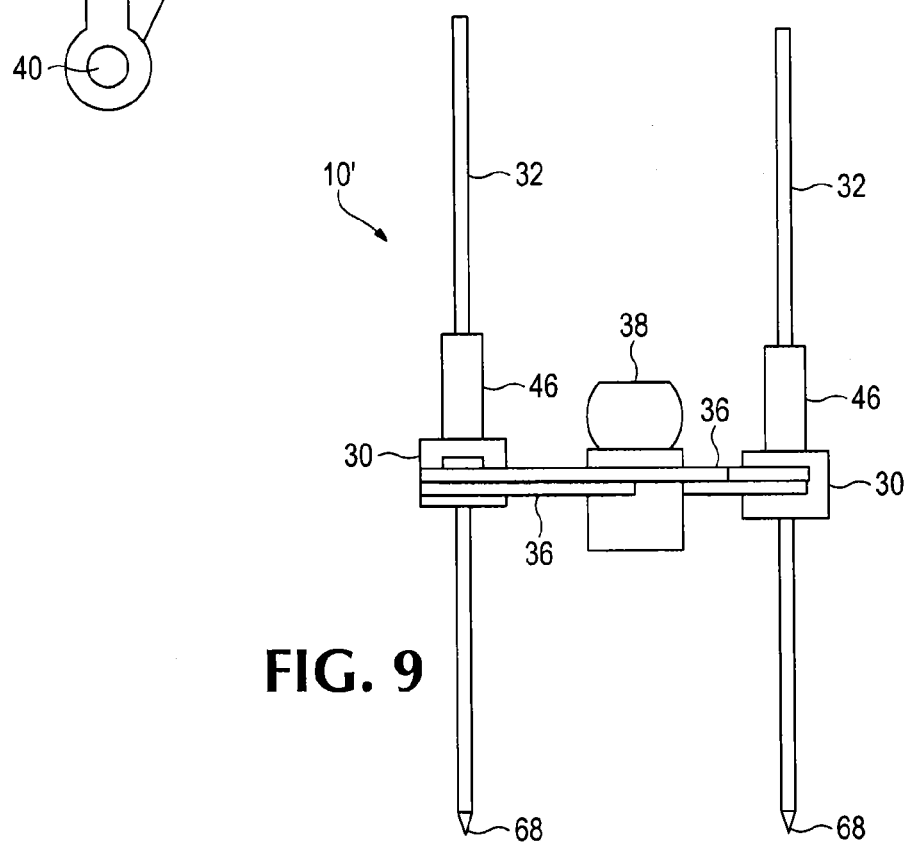
FIG. 9 is an elevational view taken from the outer end of the device shown in FIGS. 6, 7, and 8.

The point which is isometric relative to Gerdy's Tubercle is identified on the two dimensional images by determining the point on the femoral condyle which is equidistant from Gerdy's Tubercle when the joint is in full flexion and when the joint is in full extension, as shown in FIGS. 1 and 2. This point can be identified on the 2-dimensional images 17 and 19 using an ordinary compass or pair of dividers 24, ruler, or any other device suitable for measuring spatial relationships in two dimensions. The isometric point usually lies in a region near the physeal line of the caudal femoral condyle at the caudal aspect of the condyle. This region forms the isometric region in which the isometric point may be found. If a compass or divider 24 is used, the first compass or divider point is placed on Gerdy's Tubercle 20. A first "trial" point 21 is located antero-ventral to the lateral femoral fabella on the lateral femoral condyle 18, and the second point of the compass is adjusted to that distance. A first determination of the isometric region is tested on the flexed view, by maintaining the first measurement and placing the first compass 24 or divider point on Gerdy's Tubercle 20 as shown in the second image. The compass or divider is used to measure a separation distance 22 between Gerdy's Tubercle 20 and the trial point 21. By repeating this reiterative process back and forth between the images of the joint in extended and flexed positions, the isometric point is preliminarily determined. If the separation distance 22 is the same in he the flexed view and the extended view, the isometric point has been preliminarily determined. Once located, the imaged isometric point is marked on the radiographs and the distance between Gerdy's Tubercle and the imaged isometric point is measured with a specialized measuring and positioning device 10 such as that shown in FIGS. 3-5.

The device 10 is capable of fixing a location on each of two bones. The device possesses two distal ends 28 equipped with locating portions 30, each of which is associated with a marking element 32. The locating portions 30 may optionally be selectively fixable with respect to each other so that they cannot move with respect to each other. The device may also include a scale 34 capable of measuring or providing a direct indication of the distance between the two marking apparatus.

As shown in FIGS. 3-5, the device 10 possesses a main body 52 which can include a pair of arms 36 which are interconnected and extend from at least one pivot joint 40. The pivot joint 40 may include one or more rivets, pins, or other connectors. The arms 36 are connected closely to each other or to a common member by the pivot joint 40 or joints, so that they can move smoothly and precisely relative to one another. At the distal end 28 of each arm 36 is a respective locating portion 30. The locating portion 30 may include a cannulated receptacle for receiving and holding a marking element 32 such as a Steinman pin, a Kirschner wire or K-wire, or other pin, wire, tack, or any other structure capable of being affixed to bone. These marking elements 32 should be affixable to bone without a pre-drilled hole. The marking element 32 is preferably removable from the locating portion 30, but the locating portion 30 may hold the marking element 32 firmly and minimize movement of the marking apparatus. The locating portions 30 may hold the pins or wires approximately perpendicular to a plane defined by the arms of the device. At a point between the pivot joint 40 and the distal ends 28 of the arms a connecting member 37 and locking mechanism 38 may be located. In the device as shown, the connecting member 37 may be permanently attached to one arm, and may consist of a flat member mounted to one arm and extending toward and in proximity to a locking mechanism 38 which is mounted to the other arm. The locking mechanism 38 may be a thumbscrew threaded in a slot in the connecting member 37 attached to the second arm so that when tightened it fixes the distance between the arms. When the locking mechanism 38 is loosened, the arms may move freely with respect to each other. When it is tightened, they are held in a rigid or semi-rigid relationship with respect to one another. The locking mechanism 38 and connecting member 37 may serve to limit the distance to which the arms may be spread.

The device may include a scale 34 which is marked such that distance between the locating portions or marking elements may be gauged, either by trigonometrically determining the distance between the distal ends of the arms, or by specifying the angle created by the two arms at the pivot point, or by other means.

The locating portions 30 of the device may be cannulated threaded components 42 capable of receiving or holding a marking element 32 such as a pin or a wire. These components may also include locking members 44 located thereon such that their position with respect to the body or arms 36 is independently fixable, so that one locating portion 30 can thus be arranged so that it extends further below the arms 36 or body 52 than the other in order to accommodate placement on a joint having joint surfaces at different elevations with respect to each other. In FIG. 3, for example, the locating portions include externally threaded tubes 42 which are held within threads defined in an enlarged portion of the distal ends 28, and the elevation of each locating portion 30 can be changed by screwing or unscrewing the component 42. The threaded components 42 can also include rough-surfaced areas 50 that facilitate gripping so that a surgeon can easily change the elevation or position of the locating portion during surgery. The threaded cannulated components 42 may be oriented parallel with each other so that the marking elements 32 can be placed into their respective positions parallel with a hinge axis of the joint being repaired.

A device 10, shown in FIGS. 6-9 is similar to the device 10, but is somewhat simpler in structure, lacking the threaded cannulated component 42 and instead optionally having a cannulated portion 46 extending up from the distal end portions 28.

Figure 10:
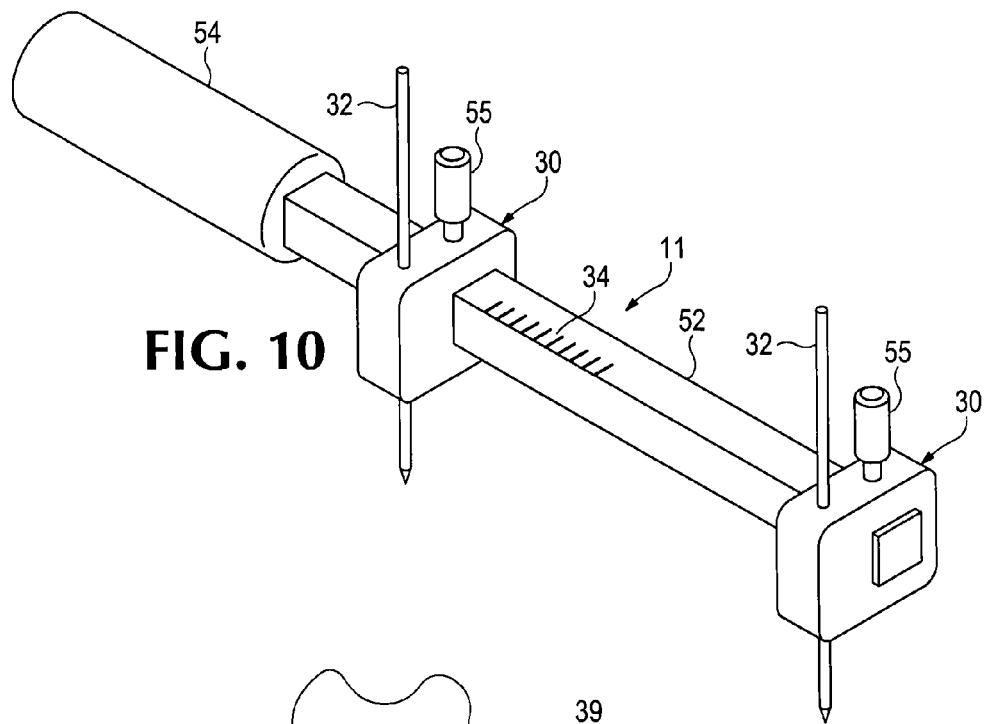
FIG. 10 is an isometric view of a measuring and positioning device which is another embodiment of an aspect of the present invention.

As shown in FIG. 10, a device 11 which is another alternative embodiment of the measuring and positioning devices 11 provides a linear member or body 52 which may be square in profile or otherwise shaped so as to keep locating portions 30 aligned with each other. The linear member or body 52 may have a handle portion 54 at one end which can be used for holding and rotating the device. The body 52 carries a pair of locating portions 30 with which marking elements 32 are associated. The position of one or more locating portions 30 is adjustable and may be lockable with locking devices 55. A scale may be associated with body 52.

To repair the stifle in which the cranial cruciate ligament has failed, once the patient is prepared for surgery, a skin incision is made extending from lateral aspect of the patella to the lateral aspect of the insertion of the straight patellar tendon on the tibial tuberosity. Subcutaneous tissues are dissected, undermined, and retracted as necessary. An incision 56 is made that extends from the lateral insertion of the straight patellar tendon along the lateral border of the straight patellar tendon proximally to the base of the patella. The joint capsule is preserved. The insertion of the fascia lata and the cranial branch of the biceps femoris muscle is identified visually and defined at Gerdy's Tubercle 20 by careful blunt dissection using a suitable instrument, such as a mosquito forceps. Another incision 57 may be made along the caudal border of the graft 12. The forceps is forced through the thin fascia at the caudal border of the biceps femoris insertion at the caudal aspect of Gerdy's Tubercle. The tissue to be used as a graft 12 is thus defined. The strongest point of insertion 58 of the graft 12 is identified at Gerdy's Tubercle 20. This point will serve as the first, or distal, proximal isometric point, indicated by the reference numeral 58 in the drawings.

Figure 11:
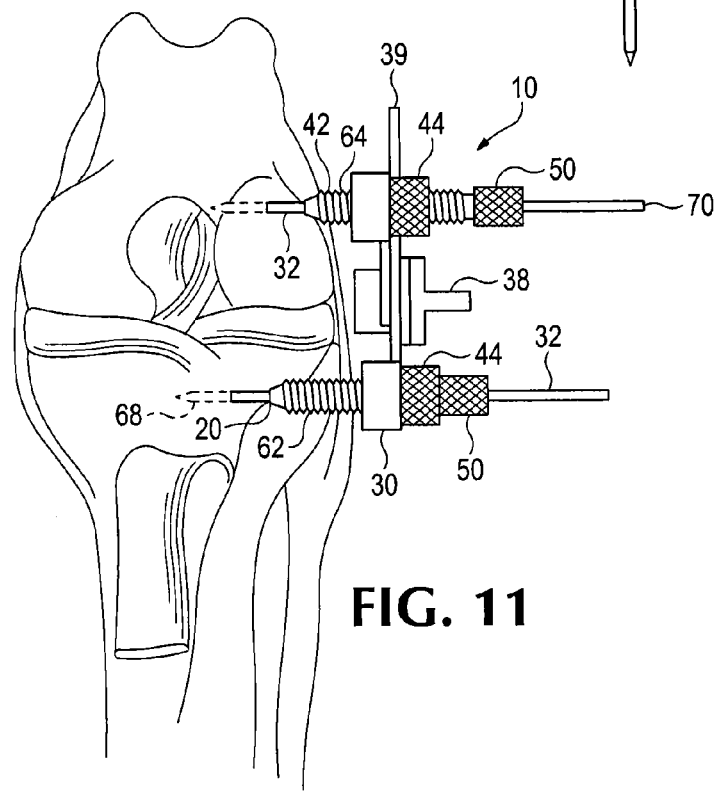
FIG. 11 is a simplified frontal view of a partially dissected stifle joint of a left leg of a canine, with the skin and other superficial tissue removed for the sake of clarity together with the device shown in FIGS. 3, 4, and 5 in use in connection with surgical repair of the stifle joint.

The measuring and positioning device 10 is aligned so that a first locating portion 62 and a marking element 32 held therein are parallel to the transverse axis of the tibial plateau and the arms of the device are parallel to the long axis of the shaft of the tibia on the frontal view, FIG. 11. The locating portions 30 and marking elements 32 should thus be parallel with each other and normal to the plane in which the tibia normally moves. The measuring and positioning device 10 is placed on the joint area so that with the measuring and positioning device aligned as previously described, the first locating portion 62 contacts Gerdy's Tubercle 20 when the second isometric point locating portion 64 contacts the lateral condyle of the femur, as shown also in FIGS. 12 and 13. A 1.5 mm (or 2 mm) K-wire 32 is then driven through the Gerdy's Tubercle locating portion 62 into Gerdy's Tubercle 20.

Figure 12:
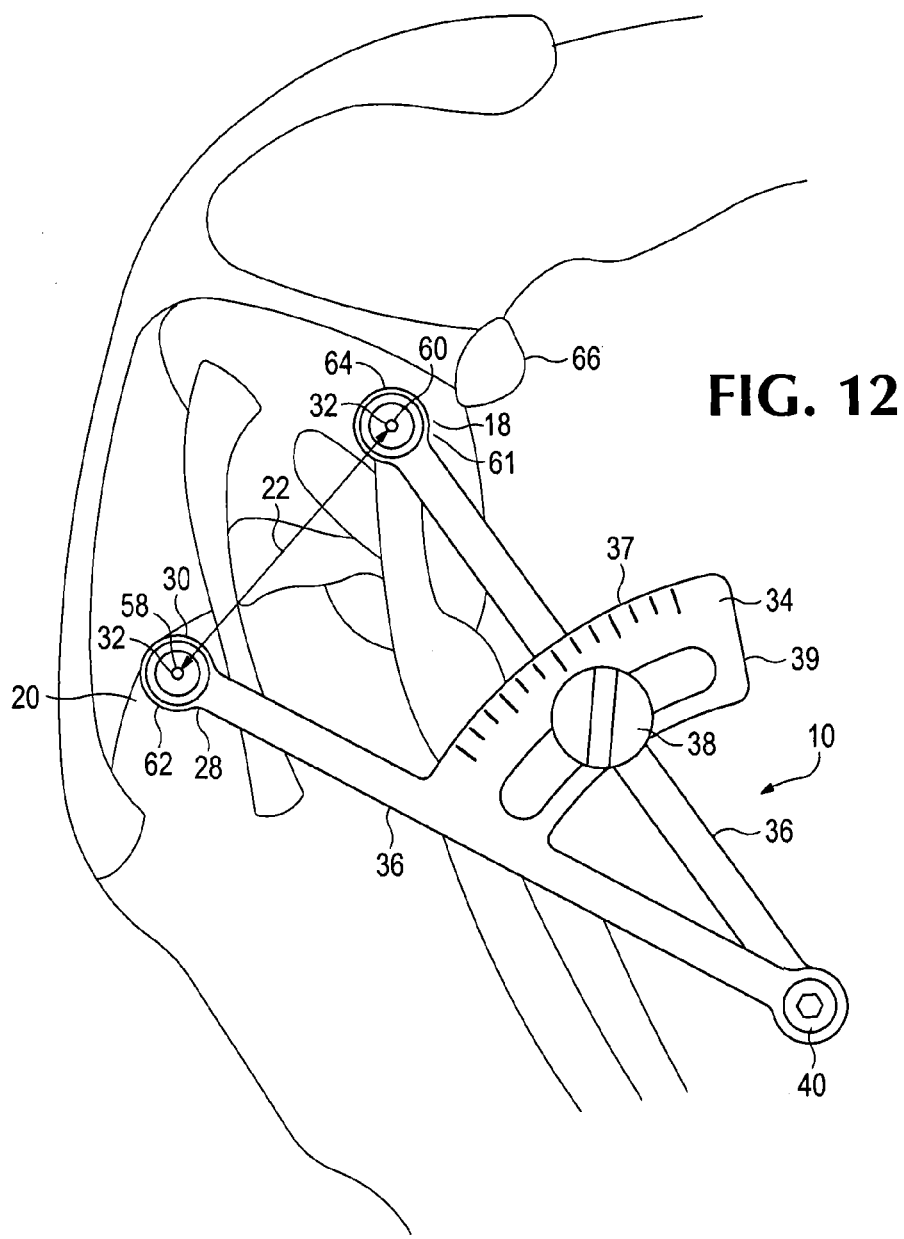
FIG. 12 is a simplified lateral view of the stifle joint of the leg shown in FIG. 11, with the skin and other superficial tissue removed for the sake of clarity, and showing the device shown in FIGS. 3, 4, and 5 in use with the stifle in a fully flexed position.
Figure 13:
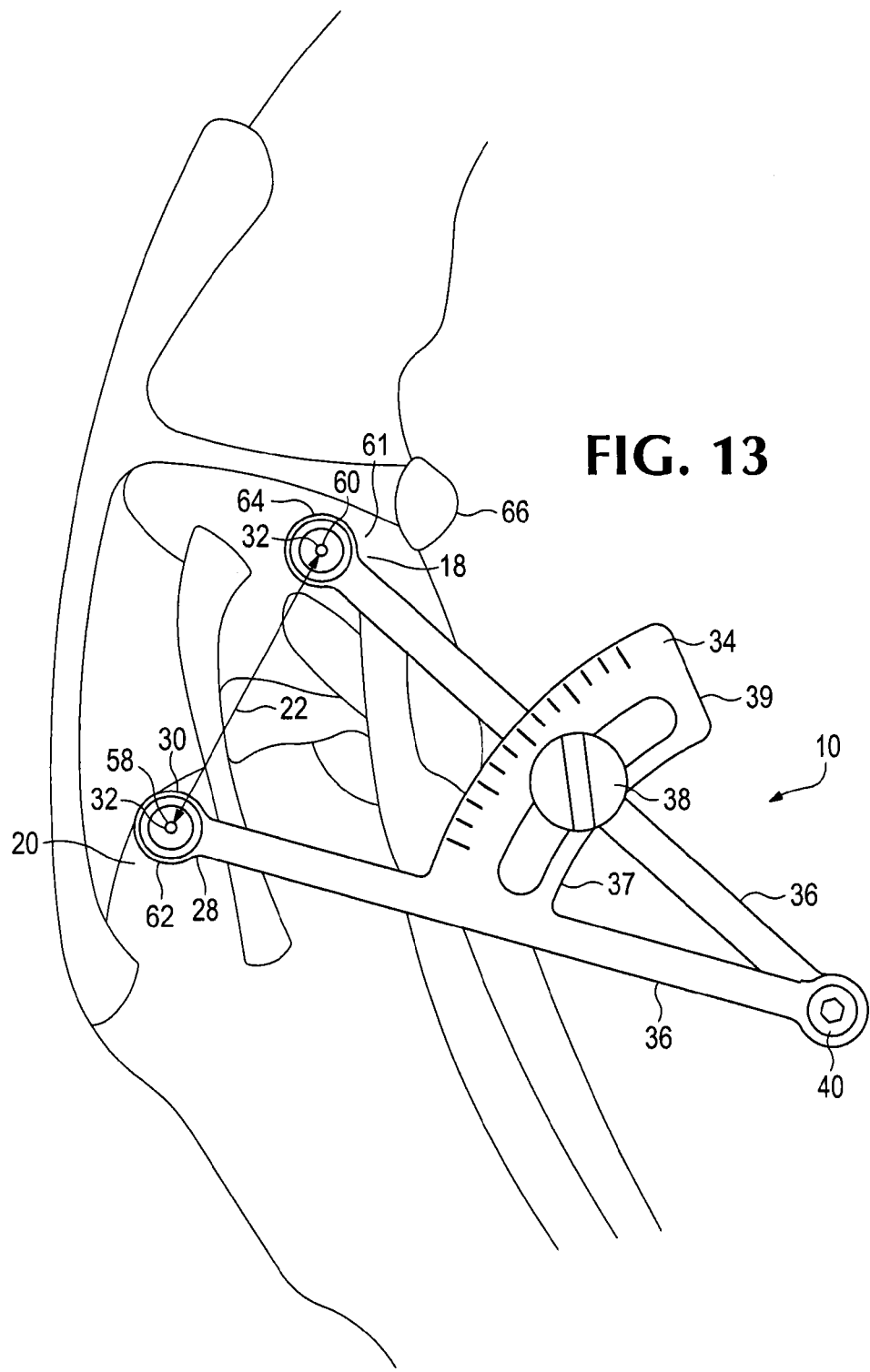
FIG. 13 is a simplified lateral view of the stifle joint of the left leg of a canine, with the skin and other superficial tissue removed for the sake of clarity, and showing the device shown in FIGS. 3, 4, and 5 in use with the stifle in a fully extended position.
Figure 14:
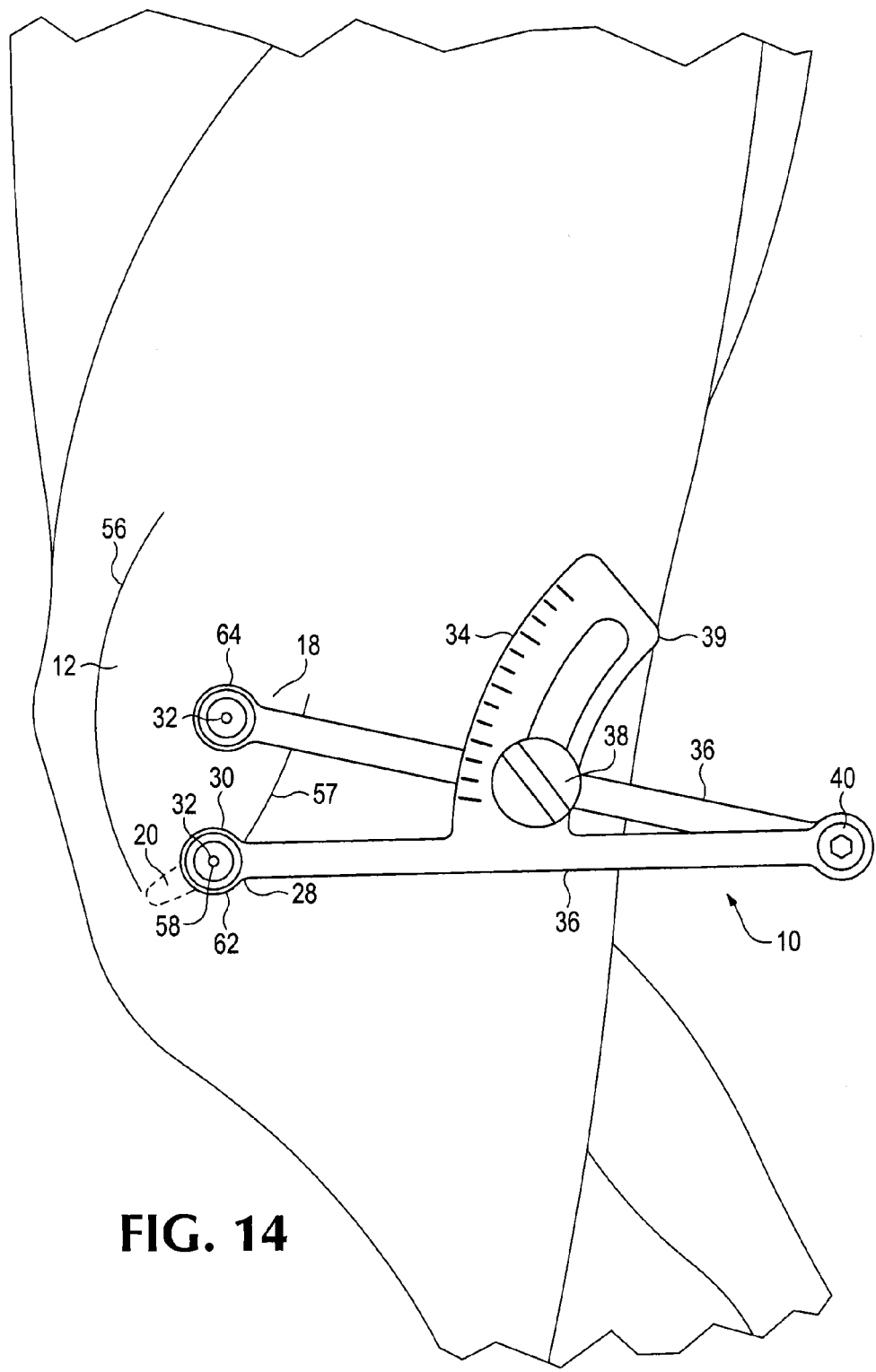
FIG. 14 is a lateral view of the stifle joint of the left leg of a canine, with skin and other superficial tissues removed for clarity, and showing use of the device shown in FIGS. 3, 4, and 5 in connection with forming an autograft to repair an injury in the joint.

At this point, it may be necessary to extend the skin incision caudally to gain additional exposure of the lateral femoral condyle. With soft tissues retracted caudally to expose the isometric region on the lateral femoral condyle, a second marking element 32 is inserted into the second locating portion 64. If a K-wire is used as the marking element 32, it should be placed so that the blunt tip 70 of the wire is down, contacting the periosteum of the lateral femoral condyle 18, which can be located initially by probing to locate the fabella 66 and the space between the fabella and the condyle 18 of the femur, and then proceeding a small distance anteriorly, referring to the radiographs 17 and 19, to locate the isometric region 61. With the device 10 set and fixed at the isometric distance previously determined by measurement of the radiographic images 17 and 19, the isometric region 61 is determined by flexing and extending the limb. The device 10 remains placed on top of the leg with the marking element 32, such as a K-wire held in the first locating portion 62 attached to the bone at Gerdy's Tubercle 20 and the marking element 32, such as another K-wire, held in the second locating portion 64 and resting against the radiographically identified isometric point, as shown in FIGS. 12 and 13. The surgeon then uses the instrument to determine whether the radiographically identified imaged isometric point is truly the actual isometric point 60. If it is, as the leg is flexed and extended the marking element 32 held in the second locating portion 64 will rest on the same place at both full extension and flexion. That is, the separation distance 22 will be the same at both full extension and full flexion.

Once the surgeon has determined the actual isometric point, the K-wire is removed and replaced in the second locating portion 64 with the sharpened tip 68 down, contacting the periosteum at the previously determined isometric point 60. The locking mechanism 38 is loosened, and the sharp end of the K-wire 68 is advanced superficially into the periosteum. Once the K-wire 60(*a*) is affixed to the bone at the isometric point, the locking mechanism 38 is loosened and the leg is again flexed and extended, and the scale 34 is observed in order to confirm that the marking member is affixed to the isometric point. If reading on the scale of the device is equal at both limits of range of motion the location of the isometric point is verified. The scale reading may decrease by about 10-15% through intermediate range of motion due to the cam configuration of the femoral condyles. This variance illustrates the relief of tension on the cruciate ligaments during the swing phase of the normal gait.

When the isometric point is identified and verified, the K-wire or other marking element 32 is driven deep into the isometric point 60 at the lateral femoral condyle 18. The device 10 and the K-wire or other marking element 32 at Gerdy's Tubercle 58 are removed. This leaves the single K-wire or other marking element 32 seated in the isometric point 60.

At this point it is possible to slide a cannulated conical periosteal burr over the K-wire at the isometric point. With superficial soft tissues retracted, the periosteum is roughened by gently rotating the burr around the K-wire with moderate pressure. The burr is withdrawn and any adherent periosteal tissue is retrieved and returned to the isometric graft site. Alternatively, the periosteum may be roughened with a sharp periosteal elevator.

A bone/tissue anchor 72 pre-threaded with two strands of suture material 76, 78 (four ends thus available) is placed into the hole created at the isometric point 60 and driven into the femoral condyle 18. While the K-wire is still seated in the bone, a cannulated anchor (not shown) can be slid down the K-wire. Otherwise, the K-wire or other marking element 32 is removed, and the hole it leaves in the bone marks the placement of the anchor. A self-tapping threaded anchor that can be nearly countersunk into the femur may be used. An appropriate suture material may be of braided ultra high molecular weight (UHMW) polyethylene, and may be non-absorbable. An example of such a suture material is Telelex, Inc.'s "Force Fiber" product. At this point in the procedure, it is advisable to perform an arthrotomy and examine intra-articular structures for damage and repair if necessary. The arthrotomy is closed with standard surgical technique.

The next step is to define the cranial proximal and distal limits of the autograft. The previous incision 56 at the lateral-most fibers of the straight patellar tendon is continued proximally to the proximal limits of the patella and the cranial border of the biceps femoris muscle. Blunt dissection separates the fascia lata from the underlying joint capsule and preserves the patellar ligament and the origin of the long digital extensor. This blunt dissection continues caudally to the isometric point 60 on the femur and frees the tissue to be used as a graft 12 from underlying soft tissue. The proximal, distal and caudal limits of the graft 12 are left undisturbed to ensure maximal blood supply and tissue strength. The fibers of the fascia lata and biceps femoris (ilio-tibial band) are traced from the anchor at the isometric point 60 on the femur to the insertion at Gerdy's Tubercle 20. The direction of these fibers determines the alignment of the graft, and fibers thus are properly aligned to form the "core" of its strength.

Figure 16:
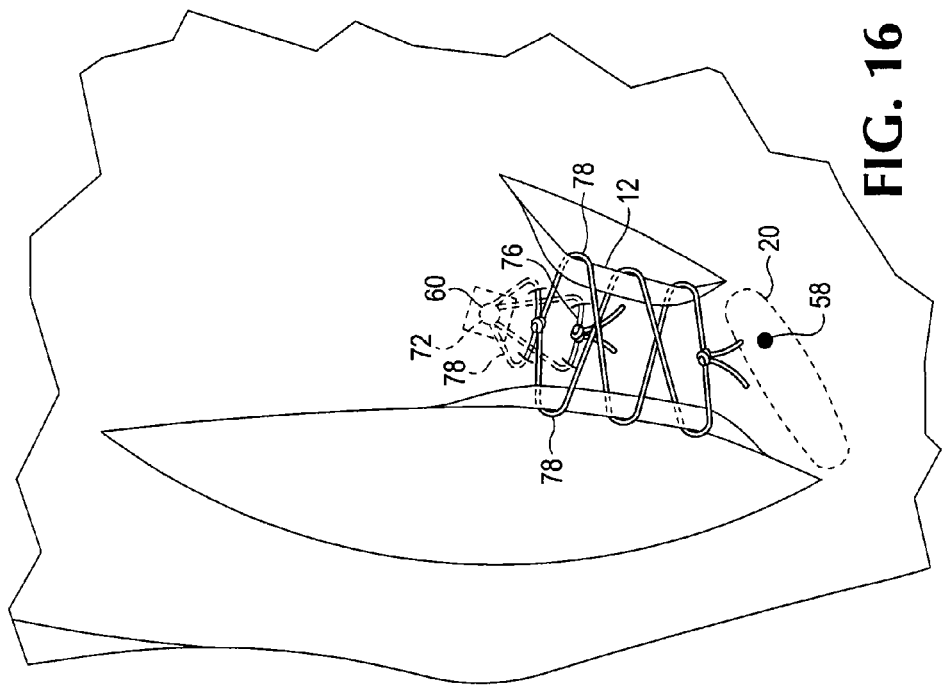
FIG. 16 is a view of the same area of the canine stifle that is shown in FIG. 15, at a subsequent step of the preparation of an autograft as part of a repair procedure.
Figure 15:
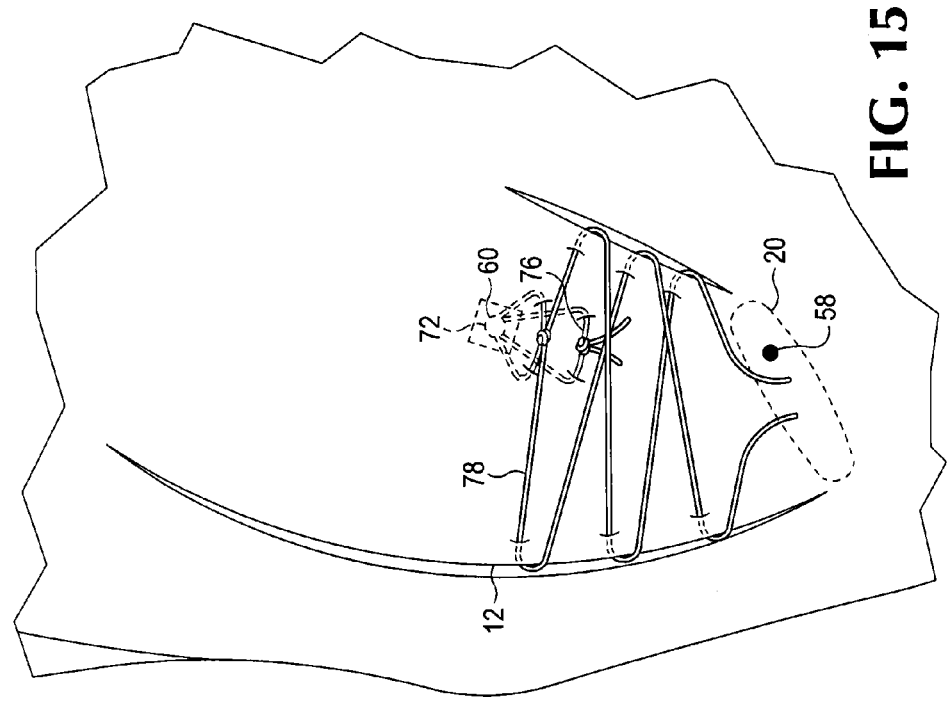
FIG. 15 is a view of a portion of a stifle joint, showing a tissue anchor in place in the femur and sutures connected with the anchor being used to attach a portion of the fascia lata to the tissue anchor.

As shown in FIGS. 15 and 16, the graft 12 is attached to the anchor 72 using the suture material 76, 78. The four suture ends are used for graft traction, graft transfixing and graft bundling sutures. The first pair of strands of anchor suture 76 are used as a "traction" suture. The stifle is placed in extension. The first set of suture strands transfix the graft 12, passing from the tissue anchor through the deep surface of the graft 12 and exiting approximately 10 mm distal to the anchor, approximately 5 mm apart, on the superficial surface of the graft 12. As the suture 76 is tightened, it will draw the graft 12 towards the anchor 72, gradually increasing the tension on the graft. As the tension is increased, drawer motion will be eliminated and the graft 12 will be drawn down into the prepared periosteal graft site 60. At this point, the stifle is tested for range of motion, stability and isometric correctness. When these criteria are met, the first "traction" suture 76 is tied. The second pair of suture strands 78 are then passed deep to the graft, exiting distal to the anchor 72 approximately 10 mm apart. Tightening these strands will place more tension on the graft, and will begin to "bundle" the graft. The second pair of traction sutures 78 are tied, but are not trimmed short, but rather, are left long for their next function, bundling, and re-enforcing the graft. The graft is "bundled" or "rolled" from a flat graft into a tube configuration with a continuous "baseball stitched" suture pattern, as shown in FIGS. 15 and 16, maintaining the previously noted alignment with the iliotibial band. Soft tissues are then closed in routine manner.

As healing occurs, the graft may undergo ligamentization, possibly due in part to the contact with the periosteum and cortical bone.

The foregoing illustration explains how the measuring device may be used to determine isometric relationships useful in repairing the cruciate ligament of a dog using an autograft formed of the fascia lata and biceps femoris. However, the device 10 may be used to determine isometric relationships during repairs of the structural ligaments in any mammal joint.

Figure 17:
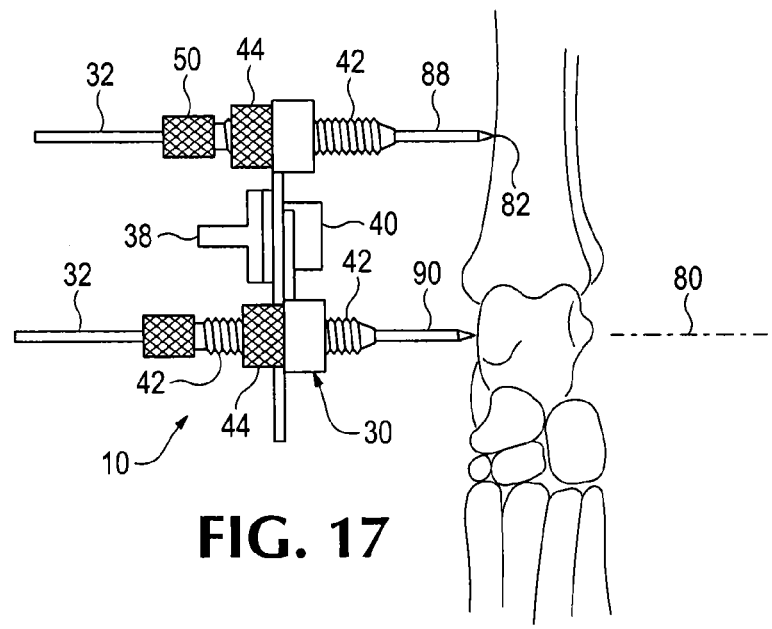
FIG. 17 is a rear elevational view of a canine hock, showing use of the device shown in FIGS. 3, 4, and 5 to identify the location of an axis of rotation of the hock joint.
Figure 18:
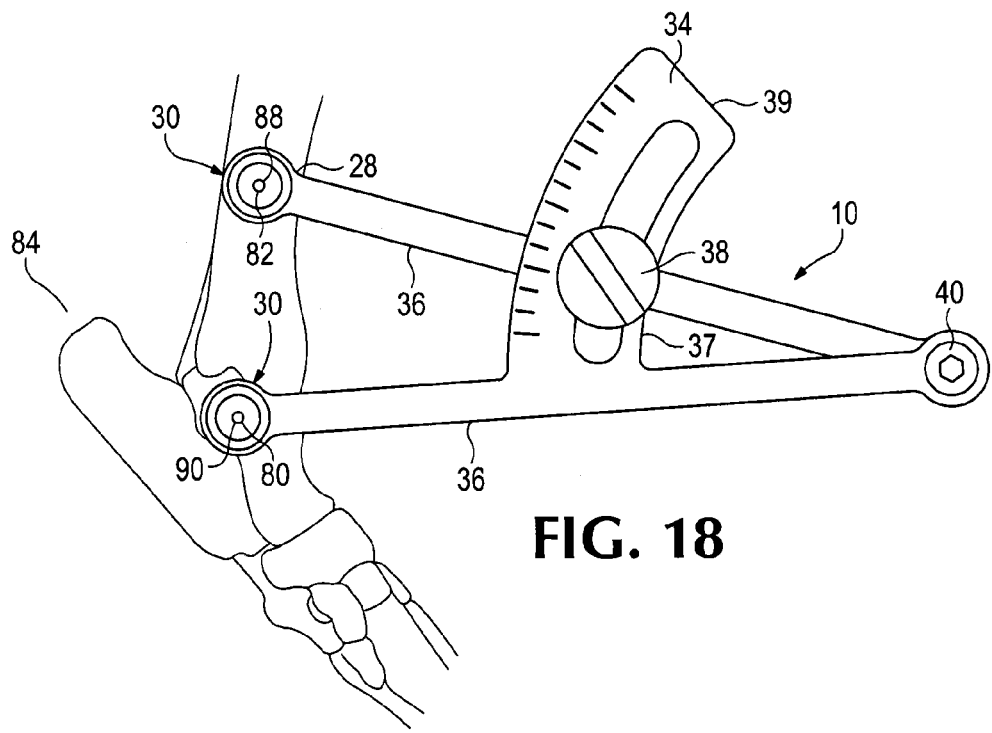
FIG. 18 is a view of the hock joint and the device shown in FIG. 17, with the device being used to identify the location of the axis of rotation of the hock.

Determination of biometric relationships may be useful for other purposes, such as determination of the axis or point of rotation of any joint that can operate in a hinge fashion, which aids in the correct replacement of external fixation devices. As illustrated in FIGS. 17 and 18, in a joint capable of moving in a hinge fashion, the center of rotation can be thought of as the center of a circle 84, with a set of reference points 82 having a type of isometric relationship with the center of rotation arrayed at the peripheral boundary of the circle 84 around the center of rotation 80. Therefore, the center of rotation of a joint may be determined with this measuring and positioning device 10. Determining the center of rotation is important when stabilizing a fracture or orthopedic condition that requires the adjacent hinged joint remain functional. Malleolar shearing injuries, for example, are commonly treated by stabilizing a hinge-type joint with a hinged external fixation device. Matching the center of rotation of the joint with the center of rotation of the hinged fixation device provides the ideal rotational relationship and maximum stability of the fracture fragments while, at the same time maintaining maximum range of motion for the joint.

The measuring device 10 can be used to locate the center of rotation 80 of a joint and guide placement of an external fixation device. First, one locating portion or marking element 88 is located at an arbitrarily chosen initial point 82 proximal or distal to the joint. This convenient location is outside the joint. Preferably, this initial reference point 82 is also the location of a transfixation pin commonly used in external fixation devices. Then, the second locating portion or marking element 90 is located in the joint approximately at the center of rotation 80 of the joint. The axis or center of rotation 80 will be a line perpendicular to the axis of the bone in which the reference point is located. Accordingly, the instrument is placed normal to the plane defined by the axis of the bone, and perpendicular to the axis of the joint. The joint is then moved through its range of motion. If the second element 90 is properly located at the center of rotation of the joint, the marking elements 88 and 90 of the device will not move toward or apart from each other when the joint is moved. If the second marking element 90 is not properly located, the movement of the joint will cause the device 10 to move, and the movement will be visible by observing the scale 34 on the device or the device itself. If the first placement of the instrument does not prove to be at the center of rotation, a different point is selected and tested until the center of rotation is identified.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A method of providing a stabilizing extracapsular surgical repair for an articulating joint between a femur and a tibia in a canine subject, comprising:
   (a) obtaining a first image showing said articulating joint in a fully flexed position and obtaining a second image showing said articulating joint in a fully extended position;
   (b) in said images identifying a pair of points between which to provide an extracapsular tension-carrying structure interconnecting said two bones, said pair of points being a reference point on said tibia and an isometric point on said femur, said reference and isometric points being located in said joint so as to be separated by a separation distance that is equal in both of said first and second images;
   (c) locating said reference point in said tibia in said articulating joint in said subject;
   (d) thereafter, locating a trial isometric point on said femur in said subject by fastening a first marking element at said reference point and holding a second marking element in said second locating portion of said device at said separation distance with said articulating joint in a first one of a fully extended position and a fully flexed position;
   (e) moving said articulating joint to the other one of said fully extended and fully flexed positions and observing whether said reference point and said trial isometric point are then separated by said separation distance; and adjusting the position of said second locating member with respect to said trial isometric point until an isometric point is located on said second one of said bones of said articulating joint; and
   (f) surgically attaching a tension-bearing repair structure to said bones so that it is attached at said reference and said isometric points so as to provide tension-bearing structure extending between respectively said reference point and said isometric point as thus located in said joint.

2. The method of claim 1, including the further step of using a scale and thereby verifying that said separation distance between said reference point and said isometric point is equal when said joint is flexed and when it is extended.

\* \* \* \* \*